(12) United States Patent
Megede

(10) Patent No.: US 10,048,256 B2
(45) Date of Patent: Aug. 14, 2018

(54) SAMPLE ANALYSIS SYSTEMS AND METHODS

(71) Applicant: Bio-Rad Laboratories, Inc, Hercules, CA (US)

(72) Inventor: Jan zur Megede, Hercules, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 86 days.

(21) Appl. No.: 15/073,518

(22) Filed: Mar. 17, 2016

(65) Prior Publication Data

US 2016/0274097 A1    Sep. 22, 2016

Related U.S. Application Data

(60) Provisional application No. 62/134,999, filed on Mar. 18, 2015.

(51) Int. Cl.
*G01N 33/543* (2006.01)
*B01L 3/00* (2006.01)
*B01L 3/02* (2006.01)

(52) U.S. Cl.
CPC ...... *G01N 33/54306* (2013.01); *B01L 3/0241* (2013.01); *B01L 3/5027* (2013.01); *B01L 3/5088* (2013.01); *B01L 2300/0861* (2013.01)

(58) Field of Classification Search
None
See application file for complete search history.

(56) References Cited

U.S. PATENT DOCUMENTS

| 6,596,546 B1 | 7/2003 | Jolley et al. |
| 2010/0190269 A1 | 7/2010 | Follonier et al. |

(Continued)

FOREIGN PATENT DOCUMENTS

| WO | 2002/071067 A1 | 9/2002 |
| WO | 2008/050274 A1 | 5/2008 |

OTHER PUBLICATIONS

Ainla, A et al., "Hydrodynamic Flow Confinement Technology in Microfluidic Perfusion Devices," Micromachines, May 10, 2012, vol. 3. pp. 443-461.

(Continued)

*Primary Examiner* — Rebecca L Martinez
(74) *Attorney, Agent, or Firm* — Kilpatrick Townsend and Stockton LLP

(57) ABSTRACT

Sample analysis systems and methods are provided. In one embodiment, the method may be achieved by applying a substance to a surface of a substrate having a first binding agent immobilized thereon; removing unbound material from at least a portion of the substrate having the substance applied thereon; applying a second binding agent to the surface of the substrate, wherein the second binding agent is optically labeled or unlabeled; removing unbound material from at least a portion of the substrate having the second binding agent applied thereon; responsive to detecting the optically labeled second binding agent bound to the substance, identifying the analyte present in the sample; and responsive to not detecting the optically labeled second binding agent bound to the substance, determining that the analyte is absent in the sample; wherein the applying the substance or second binding agent to the surface of the substrate steps are concurrent with the respective removing unbound material from at least a portion of the substrate steps. Systems and other methods are also described and illustrated.

20 Claims, 8 Drawing Sheets

(56) References Cited

U.S. PATENT DOCUMENTS

| | | |
|---|---|---|
| 2011/0105354 A1 | 5/2011 | Glezer et al. |
| 2013/0333761 A1 | 12/2013 | Delamarche et al. |
| 2015/0031145 A1* | 1/2015 | McKee .................. C07K 1/22 436/530 |
| 2015/0038355 A1 | 2/2015 | Tan et al. |

OTHER PUBLICATIONS

International Search Report and Written Opinion dated Aug. 26, 2016 in PCT/US16/22921, 18 pages.

* cited by examiner

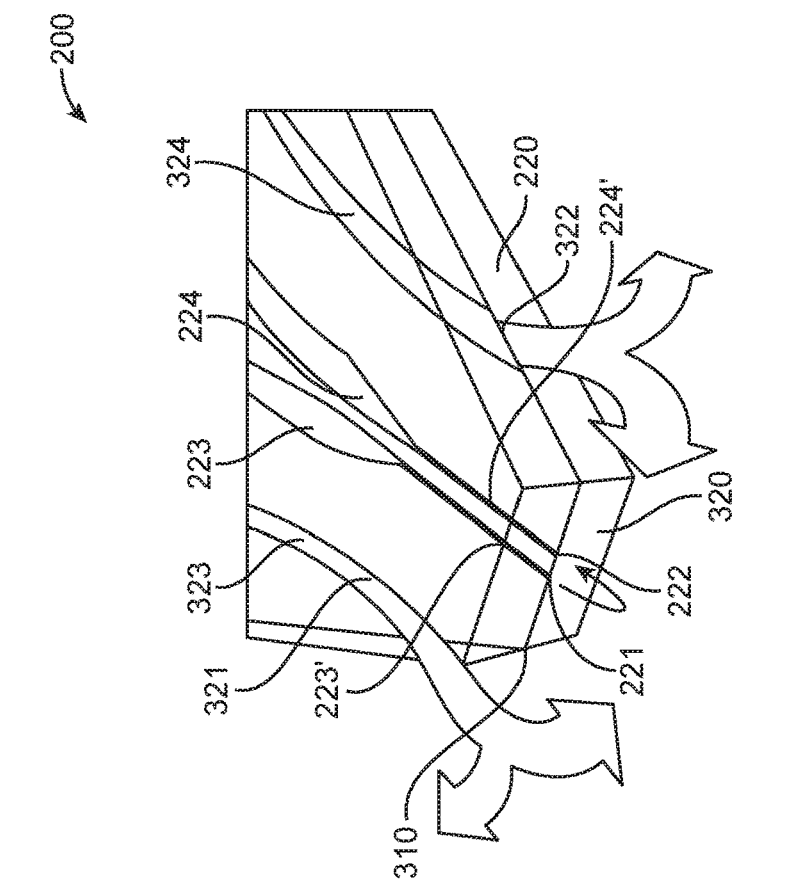
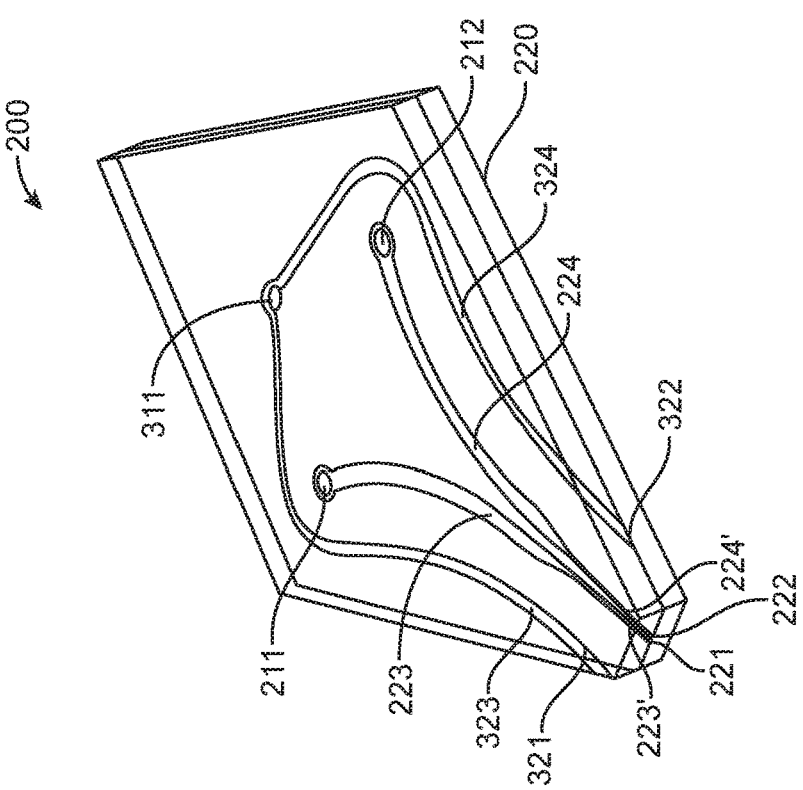
FIG. 3B (PRIOR ART)
FIG. 3A (PRIOR ART)

SAMPLE ANALYSIS SYSTEMS AND METHODS

CROSS-REFERENCES TO RELATED APPLICATIONS

This application claims priority to U.S. Provisional Application No. 62/134,999, filed Mar. 18, 2015, which is incorporated by reference herein in its entirety for all purposes.

BACKGROUND OF THE INVENTION

Enzyme-Linked ImmunoSorbent Assay ("ELISA") is a biochemical technique commonly used as a medical diagnostic tool to detect the presence of an antibody or an antigen in a sample. During an ELISA, a sample containing an analyte is subjected to a biochemical process taking place on an insoluble carrier surface such as a microwell in a microtiter plate. Depending on the particular test being conducted, a predetermined capture antibody or bio-molecule (e.g., antigen) may be immobilized on the surface of each microwell, and controlled amounts of various fluids (e.g. blocking solution, washing solution, test sample, detection antibody, primary and secondary antibodies, and substrate) may be added to the microwell according to a predetermined protocol that includes separate incubation and wash steps. The result of the biochemical process may be viewed using an optical detector measuring absorbance, fluorescence, and/or luminescence, or other properties, to provide a qualitative and/or quantitative test result.

Although ELISAs provide useful information, the technique is time consuming due to the long incubation times during each assay step. The antibodies and reagents used in ELISAs are also expensive.

BRIEF SUMMARY OF THE INVENTION

Disclosed herein are sample analysis systems and methods of using such systems.

In an embodiment, a method is disclosed in which the presence or absence of a analyte in a sample is determined. The method comprises applying a substance to a surface of a substrate having a first binding agent immobilized thereon, wherein the first binding agent is capable of binding to the substance; removing unbound material from at least a portion of the substrate having the substance applied thereon; applying a second binding agent to the surface of the substrate, wherein the second binding agent is optically labeled or unlabeled; removing unbound material from at least a portion of the substrate having the second binding agent applied thereon; and responsive to detecting an optically labeled second binding agent bound to the substance, identifying the analyte present in the sample; and responsive to not detecting the optically labeled second binding agent bound to the substance, determining that the analyte is absent in the sample; wherein the applying the substance or second binding agent to the surface of the substrate steps are concurrent with the respective removing unbound material from at least a portion of the substrate steps. In some embodiments, the method further includes applying a third binding agent to the surface of the substrate having the second binding agent bound to the substance, wherein the third binding agent is optically labeled and the second binding agent is optically unlabeled; removing unbound material from at least a portion of the substrate having the third binding agent applied thereon; responsive to detecting an optically labeled third binding agent bound to the second binding agent, identifying the analyte present in the sample; and responsive to not detecting the optically labeled third binding agent bound to the second binding agent, determining that the analyte is absent in the sample, wherein the applying the third binding agent to the surface of the substrate step is concurrent with the removing unbound material from at least a portion of the substrate step.

In some embodiments, a system for determining the presence or absence of an analyte in a sample includes a substrate having a first binding agent immobilized in discreet locations, wherein the first binding agent is capable of binding to a substance applied to the surface of the substrate; a dispenser configured to simultaneously dispense the substance or at least one binding agent onto the substrate and to remove unbound material from the substrate; a light source configured to illuminate the surface of the substrate; and a detector configured to detect the presence or absence of the at least one binding agent.

In an embodiment, a method of determining the presence or absence of a analyte in a sample comprises applying a first binding agent to the surface of the substrate having a substance immobilized thereon, wherein the first binding agent is capable of binding to the substance and is optically labeled or unlabeled; removing unbound material from at least a portion of the substrate having the first binding agent applied thereon; and responsive to detecting an optically labeled first binding agent bound to the substance, identifying the analyte present in the sample; and responsive to not detecting the optically labeled first binding agent bound to the substance, determining that the analyte is absent in the sample; wherein the applying the first binding agent to the surface of the substrate step is concurrent with the removing unbound material from at least a portion of the substrate step. In some embodiments, the method further includes applying a second binding agent to the surface of the substrate having a first binding agent bound to the substance, wherein the second binding agent is optically labeled and the first binding agent is optically unlabeled; removing unbound material from at least a portion of the substrate having the second binding agent applied thereon; responsive to detecting the second binding agent bound to the first binding agent, identifying the analyte present in the sample; and responsive to not detecting the second binding agent bound to the first binding agent, determining that the analyte is absent in the sample.

In some embodiments, a system for determining the presence or absence of an analyte in a sample includes a substrate having a substance immobilized in discreet locations, wherein an first binding agent is capable of binding to the substance; a dispenser configured to simultaneously dispense at least one binding agent onto the substrate and to remove unbound material from the substrate; a light source configured to illuminate the surface of the substrate; and a detector configured to detect the presence or absence of the at least one binding agent.

In an embodiment, a method of determining the presence or absence of a analyte in a sample comprises applying a mixture of a substance and a sample having an analyte to a surface of a substrate having a binding agent immobilized thereon, wherein the binding agent is capable of binding to the substance and the analyte; removing unbound material from at least a portion of the substrate having the binding agent immobilized thereon; and responsive to not detecting the substance bound to the binding agent, identifying the analyte present in the sample; and responsive to detecting the substance bound to the binding agent, determining that the analyte is absent in the sample; wherein the applying the mixture to the surface of the substrate step is concurrent with the removing unbound material from at least a portion of the substrate step.

In some embodiments, a system for determining the presence or absence of an analyte in a sample includes a substrate having a binding agent immobilized in discreet locations, wherein the binding agent is capable of binding to an analyte in a sample and to a substance; a dispenser configured to simultaneously dispense a mixture of the sample and the substance onto the substrate and to remove unbound material from the substrate; a light source configured to illuminate the surface of the substrate; and a detector configured to detect the presence or absence of the analyte in the sample bound to the binding agent.

The application of the substance/second binding agent to the surface of the substrate and wash steps may be performed with a hydrodynamic flow confinement dispenser. In an embodiment, the hydrodynamic flow confinement dispenser is a microfluidic probe. In an embodiment, the hydrodynamic flow confinement dispenser is a microfluidic probe having multiple microchannels. In another embodiment, the hydrodynamic flow confinement dispenser is an array of microfluidic probes.

In some embodiments, the surface of the substrate is wet. In an embodiment, the substance or binding agent is dispensed onto the surface of the substrate dispensing in at least one discreet spot. In some embodiments, the spot is from about 25 nanometers to about 500 micrometers in diameter. In an embodiment, the substances/binding agents are dispensed in at least one discreet path. In certain embodiments, the path is a straight line. In some embodiments, the path is from about 25 nanometers to about 500 micrometers wide. In some embodiments, 1-100 substances/binding agents are bound to the surface of the substrate.

In some embodiments, the substance or binding agent is an antigen, an antibody or an antibody fragment from a reagent or sample. In some embodiments, the sample is selected from a group consisting of cell extract, whole blood, plasma, serum, saliva, urine, milk, eggs and water. In certain embodiments, the sample includes an analyte selected from the group consisting of hormones, proteins, peptides, antibodies and antibody fragments.

BRIEF DESCRIPTION OF THE DRAWINGS

FIGS. 3A and 3B show a microfluidic probe of the prior art.

DEFINITIONS

The term "optically labeled binding agent" refers to a binding agent labeled with a luminescent (e.g., fluorescent, colorimetric, phosphorescent or chemiluminescent) label that, when irradiated with light, emits an optical signal.

DETAILED DESCRIPTION OF THE INVENTION

Described herein are systems and methods for analyzing samples. An automated high throughput system and method of sample analysis has been discovered that can test multiple samples at once, uses lower amounts of reagents, and can provide quick test results.

Advantages of the systems and methods described herein include, but are not limited to: (1) providing systems that are compact in size and that deliver nanoliter to microliter volumes of reagents (e.g., solutions containing an antigen or an antibody); (2) providing systems that localize the reaction chemistry and decrease reaction time; (3) providing systems capable of performing multiplex assays (e.g., testing multiple samples for a single analyte and/or testing a single sample for multiple analytes); (4) providing systems that are "hands-free"; (5) providing systems in which the application of reagents or samples and washing of unbound material steps may be performed simultaneously.

As used in this specification and the appended claims, the singular forms "a", "an", and "the" include plural referents unless the content clearly dictates otherwise. Thus, for example, reference to a system comprising "a binding agent" includes a system comprising one or more binding agent. Likewise, reference to "a substance" includes one or more substances.

Systems

Figure 1:
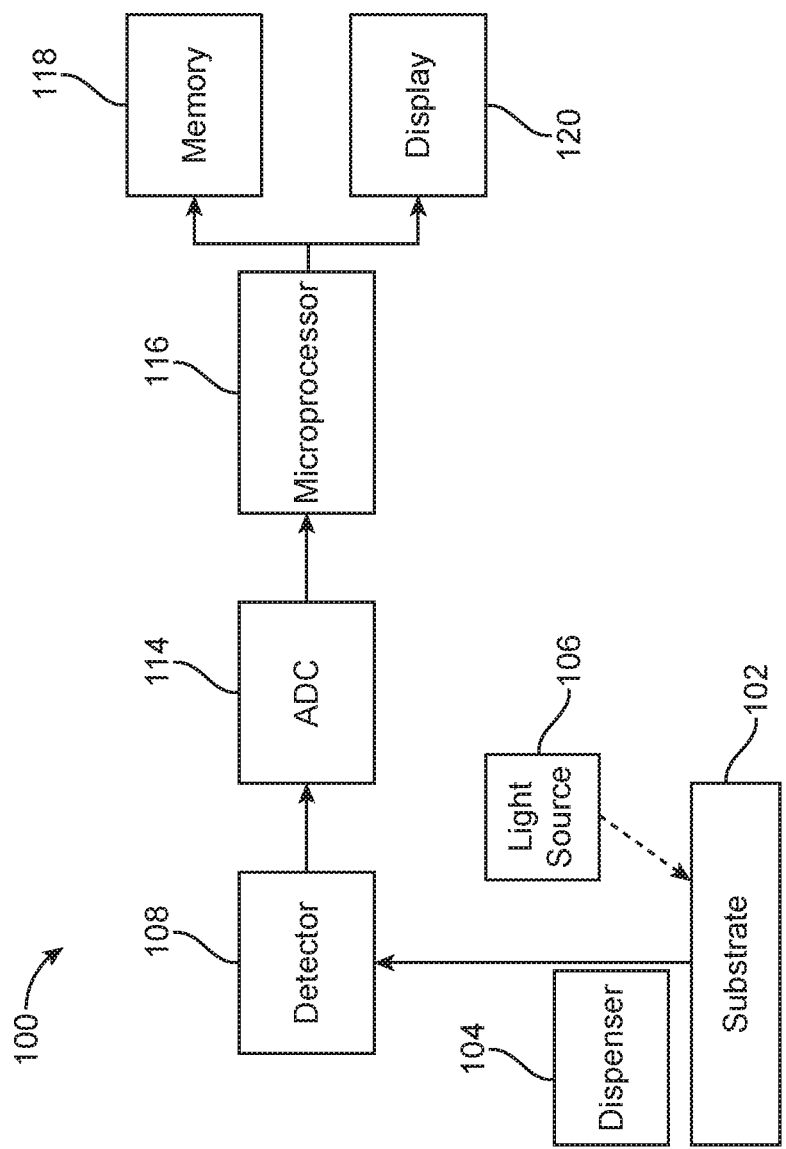
FIG. 1 shows a schematic view of a sample analysis system according to an embodiment of the invention.

Referring to FIG. 1, a system 100 for analyzing samples is illustrated. In an embodiment, the system 100 is used to apply a substance (i.e., an antigen or an antibody from a reagent or a sample) to a substrate having at least one binding agent (i.e., antibodies or antigens from a sample or a reagent, respectively) thereon. The system 100 includes a substrate 102, a dispenser 104 (e.g., a microfluidic probe), a light source 106 and a detector 108.

The substrate 102 provides a surface onto which a binding agent 110 (shown in FIG. 2) is immobilized or bound. The substrate 102 is generally planar in shape and may be formed of one or more materials including, but not limited to, polyethylene terephthalate (e.g., Mylar), polypropylene, polystyrene, polycarbonate, plastic, glass, silicon, silicon oxide, and/or metals and metal oxides either bare or functionalized with polymers. The substrate 102 may contain microwells or nanowells. Examples of polymers with which to functionalize the surface of substrates formed from metal or metal ozide include glycidoxypropyltriethoxysilane, poly-L-lysine, polybrene, polyethylene glycol polymers, dextran polymer, aminopropylsilane, caroxysilane, hydrogels and polymer brushes, and/or self-assembled monolayers of e.g. functionalized alkyl thiols, dendrimers or oligonucleotides. In an embodiment, the substrate 102 is coated with gold. In an embodiment, the substrate 102 is a microtiter plate having a plurality of wells in which the samples 110 may be immobilized. In some embodiments, the substrate 102 is a membrane formed of material including, for example, nitrocellulose, polyvinylidene fluoride, nylon or polysulfone.

The surface of the substrate 102 may be wet or dry. A wet surface is desirable in some embodiments in which the binding agents 110 require hydration to remain active. Exemplary fluids used to wet the surface of the substrate 102 include, but are not limited to, buffer, water, saline, blocking solution, and/or oil (e.g., mineral oil).

In some embodiments, the substrate 102 is mounted on a platform that is moveable in the X-Y- and/or Z direction.

Figure 2:
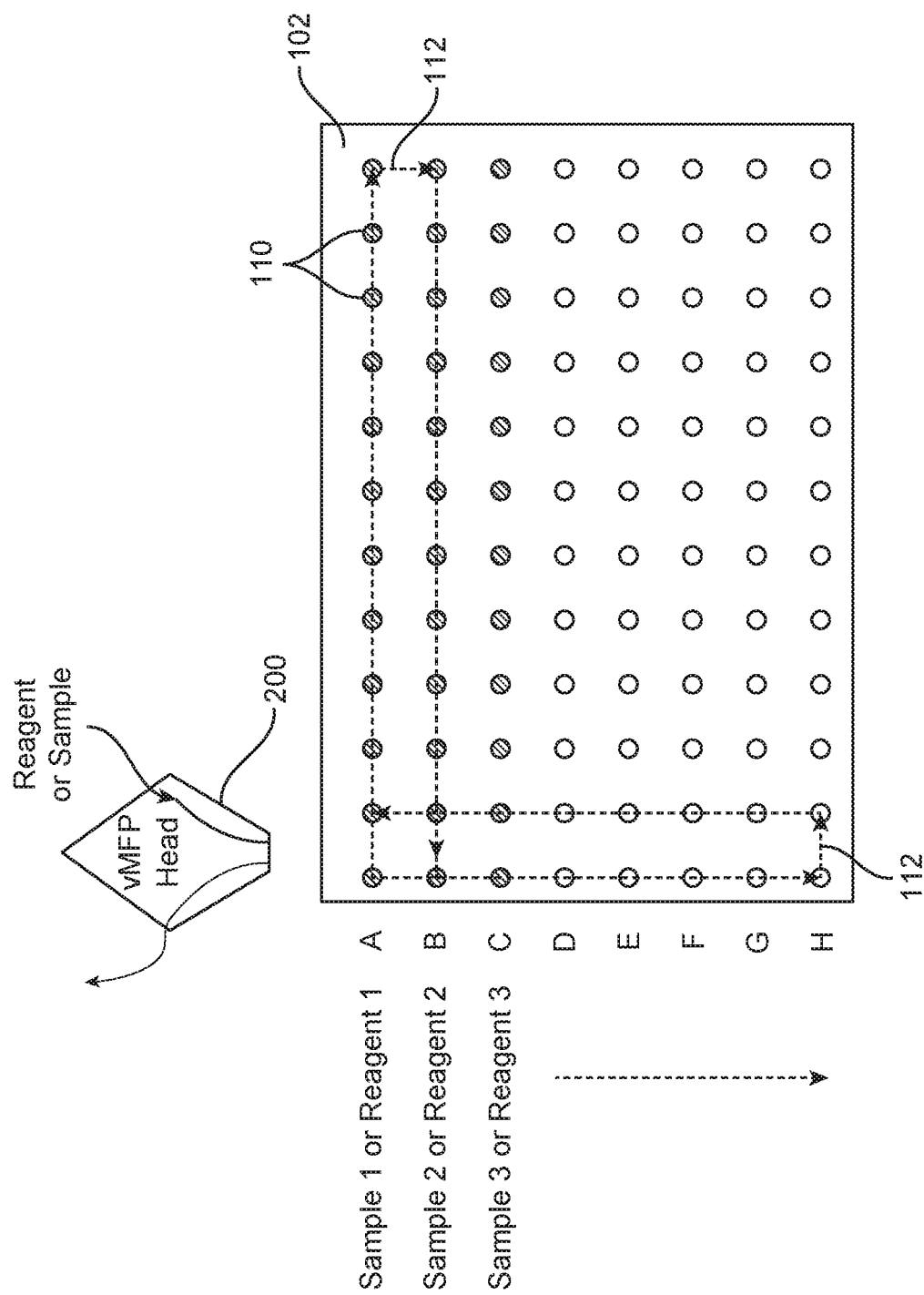
FIG. 2 shows a top view of a substrate having an array of binding agents (e.g., samples or reagents) applied thereon in which a substance (e.g., a reagent or a sample, respectively), is applied with a microfluidic probe according to an embodiment of the invention.

In an embodiment illustrated in FIG. 2, one or more binding agents 110 are bound to a surface of the substrate 102 in a pattern of spots and/or dots. In an embodiment, the spots/dots are about 25 nanometers to about 500 micrometers in diameter. In certain embodiments, the spots/dots are about 50 nanometers to about 200 micrometers diameter. In an embodiment, an array of spots and/or dots covers a surface of the substrate 102. In some embodiments, one or more binding agents 110 are bound to the substrate 102 in an array of lines. In an embodiment, the lines are about 25 nanometers to about 500 micrometers wide. In certain embodiments, the lines are about 50 nanometers to about 200 micrometers wide. In an embodiment, the array of lines spans the width of the substrate 102. In another embodiment, the array of lines spans the length of the substrate 102. In some embodiments, 1-100 binding agents are bound to the surface of the substrate 102. In certain embodiments, 10-100 binding agents are bound to the surface of the substrate. In some embodiments, 10-50 binding agents are bound to the surface of the substrate. The binding agents 110 may be the same or different.

The binding agents 110 are capable of binding to a substance (e.g., an analyte) in a sample or to a substance (e.g., an antibody or antigen) in a reagent. Exemplary binding agents 110 may include, but are not limited to, antigens, antibodies and/or antibody fragments. Exemplary analytes may include, but are not limited to, hormones, bacterial antigens, antibodies, antibody fragments, proteins and/or peptides. In some embodiments, the substance (or analyte) is an antibody to an antigen and the binding agent 110 is the antigen. In some embodiments, the substance is an antigen (which may be recombinant antigens) and the binding agent 110 is an antibody to the antigen. Exemplary samples include, but are not limited to whole blood, plasma, serum, saliva, urine, milk, eggs, ascites, hybridoma supernatant, cell lysate, tissue or cell culture supernatant, and/or water.

In embodiments in which the binding agent or substance is an antibody, the antibody may be polyclonal and/or monoclonal or a mixture of monoclonals of differing antigenic specificities or functional fragments thereof, which include the domain of a F(ab')2 fragment, a Fab fragment and scFv. A functional antibody fragment can be (i) derived from a source (e.g., a transgenic mouse); or (ii) chimeric, wherein the variable domain is derived from a e.g. non-human origin and the constant domain is derived from a e.g. human origin or (iii) complementary determining region (CDR)-grafted, wherein the CDRs of the variable domain are from a e.g. non-human origin, while one or more frameworks of the variable domain are of e.g. human origin and the constant domain (if any) is of e.g. human origin. The antibodies can be isolated from natural source, i.e. living organism or cell culture or can be fully or partially synthetic antibodies. A synthetic antibody is an antibody having a sequence derived, in whole or in part, in silico from synthetic sequences that are based on the analysis of known antibody sequences. In silico design of an antibody sequence or fragment thereof can be achieved, for example, by analyzing a database of antibody or antibody fragment sequences and devising a polypeptide sequence utilizing the data obtained therefrom. The antibody may also be one or more primary and/or secondary antibodies.

The binding agents 110 may be deposited onto the surface of the substrate 102 by techniques such as, but not limited to, hydrodynamic fluid confinement, ink jet printing, spray deposition, microspotting and/or microcontact printing. During or after deposition, the binding agents 110 may be immobilized onto the surface of the substrate 102 by, for example, electrostatic attractions, affinity interactions, hydrophobic/hydrophilic interactions, or covalent coupling.

In some embodiments, regions of the substrate 102 that do not have immobilized binding agents 110 and could provide non-specific binding sites may be treated with blocking agents such as, for example, non-fat milk protein, casein, and/or bovine serum albumin in a buffer.

Referring again to FIG. 1, the dispenser 104 is configured to dispense a microfluidic or sub-microfluidic volume of one or more binding agents or substances (i.e., reagents or samples) in a discreet path 112 on top of the binding agents 110. In some embodiments, the path 112 is continuous. In some embodiments, the path 112 is discontinuous. In some embodiments, the path spans the length of the substrate 102. In other embodiments, the path spans the width of the substrate 102. In certain embodiments, the width of the path is from about 50 nanometers to about 200 micrometers wide. In some embodiments, 1-100 binding agents/substances are dispensed in parallel paths on the surface of the substrate 102. In other embodiments, 10-100 binding agents/substances are dispensed in parallel paths on the surface of the substrate 102. In some embodiments, 10-50 binding agents/substances are dispensed in parallel paths on the surface of the substrate 102. In some embodiments, one or more binding agents/substances are dispensed in a pattern of spots and/or dots. In an embodiment, the binding agents/substances spots/dots are about 25 nanometers to about 500 micrometers in diameter. In certain embodiments, the binding agents/substances spots/dots are about 25 nanometers to about 200 micrometers in diameter. In an embodiment, an array of binding agents/substances spots and/or dots covers a surface of the substrate.

In some embodiments, the dispenser 104 is moveable in the X-Y- and/or Z direction. Movement and functions of the dispenser 104 may be computer controlled.

In some embodiments, the dispenser 104 is a hydrodynamic flow confinement dispenser. In an embodiment, the hydrodynamic flow confinement dispenser is a microfluidic probe 200 (or vertical MFP) as described in U.S. patent application Ser. No. 13/881,989, which is incorporated by reference in its entirety herein. In an embodiment illustrated in FIGS. 3A and 3B, the microfluidic probe 200 may include a base layer 220, wherein processing liquid microchannels 223, 224 are provided together with immersion liquid microchannels 323, 324. Each channel is in fluid communication with an aperture 221, 222, 321, 322, each aperture located on a face of the base layer (not necessarily the same face), and preferably in close proximity. The channels 223, 224, 323, 324 also provide connection between motorized pumps and the apertures 221, 222, 321, 322. When moving the microfluidic probe 200 in the vicinity of a surface, processing liquid provided through the aperture 221 will combine with the immersion liquid and preferably inserts into immersion liquid provided via the apertures 321 and 322, as symbolized by the curved (thick) arrows if FIG. 3B. The latter are provided for the sake of understanding; their dimension are deliberately exaggerated. In this regard, in some embodiments, the device is configured to obtain a laminar flow. In some embodiments, an aperture dimension may be tens of micrometers e.g., 10-50 micrometers). In some embodiments, the aperture dimension may be 1-50 micrometers. The apertures are typically spaced apart by hundreds of micrometers (e.g., 200-500 micrometers). As pairs of processing channels/apertures are used herein, the processing liquid can be re-aspirated at aperture 222 together with some of the immersion liquid. Note that the flow path between apertures 221 and 222 can be inverted, i.e. processing liquid can be injected from aperture 222 while aperture 221 can aspirate liquid. The processing liquid can be essentially located nearby the apertures 221 and 222 and is surrounded by an immersion liquid that is essentially present in the vicinity of the head 200. A cover layer 210 closes the channels open on the upper face of the base layer, as depicted.

In addition, in some embodiments, portions of the processing liquid microchannels are provided as grooves 223', 224' in the layer thickness of the base layer 220, open on the upper face thereof. This way, forming a microchannel is easily achieved, in spite of its transverse dimensions (likely small, e.g., a few tens of micrometers). After assembly, the groove is closed by a portion of the cover layer 210. The groove may be engraved by a tool directly on the upper surface of the base layer 220. It can have any appropriate section shape, e.g. rounded, square, U or V section. The tool can be chosen according to the material of the base layer 220. In a variant, laser ablation can be contemplated. Most advantageously yet, deep reactive ion etching (DRIE) is used for fabrication of microchannels.

As depicted in FIG. 3B, the grooves 223', 224' extend up to respective apertures 221, 222. Similarly, immersion channels 223, 224 reach respective apertures 321, 324. In this example, channels and apertures are symmetrically arranged around the main axis of the upper face of the head. An aperture is directly formed at an end of the groove at the level of an edge 310 of the front face 320 of the base layer 220, which here again is easily machined. Said front end 320 is typically made acute, which allows for compact liquid deposition on a surface of interest, and leaves rooms for easy optical monitoring.

Referring to FIG. 3A, vias 211, 212 are provided on the cover layer 210. An additional via 311 is shown, which allows for relaying fluid communication to immersion channels 323, 324 (only one via is provided here, which feeds both immersion channels). Corresponding tubing ports connected to the vias can be provided (not shown). The channels have ends arranged such as to face the vias.

As depicted in FIGS. 3A and 3B, the microfluidic probe 200 includes two processing liquid microchannels. In some embodiments, the microfluidic probe 200 includes more than two processing liquid microchannels. In some embodiments, the microfluidic probe 200 may include 2-50 processing liquid microchannels (see FIG. 4). In some embodiments, the microfluidic probe 200 may include a heating element in at least one of the processing liquid microchannels. Heating the sample may increase the speed at which the antigens and antibodies react which may reduce test time.

Figure 5:
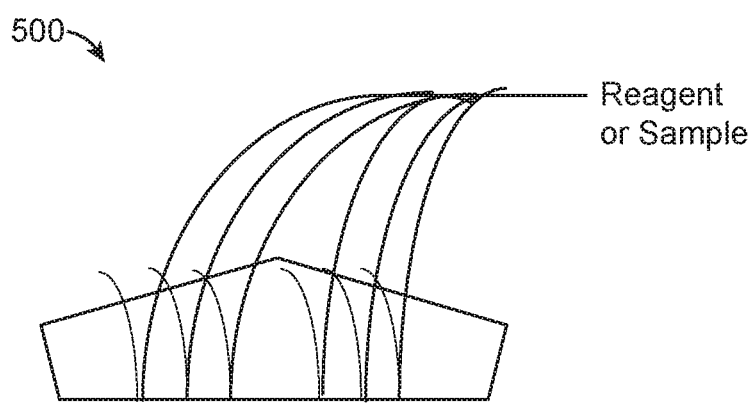
FIG. 5 shows multiple microfluidic probes in parallel connected to a single or multiple reagent solutions according to an embodiment of the invention.

In an embodiment illustrated in FIG. 5, the microfluidic probe is an array of probes connected in parallel (i.e., probe array 500) which may be connected to the same or different processing liquids. In another embodiment, each of the probes in the probe array 500 includes a plurality of microchannels.

Microfluidic probes may be formed of material that is compatible with the fluids flowing through the channels. Exemplary compatible materials include, but are not limited to, silicon, silica, polydimethylsiloxane (PDMS), gallium arsenide, glass, ceramics, quartz, polymers such as neoprene, Teflon™, polyethylene elastomers, polybutadiene/SBR, nitrites, nylon, and/or metals. The inner surface of the channels may also be coated with suitable material to reduce the affinity between the fluid components and the channels themselves.

Exemplary processing liquids include reagents, samples, buffer, blocking solution, oil (e.g., mineral oil) and/or air. Exemplary immersion liquids include buffer, blocking solution, and oil.

The processing and immersion liquids are configured to fill the microchannels in an efficient and reproducible manner. As such, the liquids are formulated to have an appropriate viscosity, hydrophilicity or hydrophobicity. In some embodiments, the liquids may include one or more surfactants, detergents, emulsifiers, solubilizers, to provide acceptable/optimal filling of the microchannels in a fast and reproducible manner. In some embodiments, the liquids comprise one or more of: ammonium lauryl sulfate, sodium lauryl sulfate (SDS, sodium dodecyl sulfate), sodium laureth sulfate, sodium myreth sulfate, dioctyl sodium sulfosuccinate, perfluorooctanesulfonate (PFOS), perfluorobutanesulfonate, linear alkylbenzene sulfonates (LABs), sodium stearate, sodium lauroyl sarcosinate, perfluorononanoate, perfluorooctanoate, alkyltrimethylammonium salts (e.g., cetyl trimethylammonium bromide), cetylpyridinium chloride (CPC), benzalkonium chloride (BAC), benzethonium chloride (BZT), 5-Bromo-5-nitro-1,3-dioxane, dimethyldioctadecylammonium chloride, cetrimonium bromide, dioctadecyldimethylammonium bromide (DODAB), CHAPS, cocamidopropyl hydroxysultaine, lecithin, polyoxyethylene glycol alkyl ethers, polyoxypropylene glycol alkyl ethers, glucoside alkyl ethers, polyoxyethylene glycol octylphenol ethers (e.g., Triton X-100), Polyoxyethylene glycol alkylphenol ethers, glycerol alkyl esters, polyoxyethylene glycol sorbitan alkyl esters (e.g., Polysorbate), sorbitan alkyl esters, cocamide MEA, cocamide DEA, dodecyldimethylamine oxide, block copolymers of polyethylene glycol and polypropylene glycol and/or polyethoxylated tallow amine (POEA).

In some embodiments, the liquids comprise tailored concentrations of Tween (e.g., Tween-20) and bovine serum albumin (BSA). In some embodiments, concentrations of Tween (e.g., Tween-20) and BSA are designed to provide for efficient flowing of solutions for the length of the microchannels. In some embodiments, concentrations of Tween (e.g., Tween-20) and BSA are designed to provide activation/wetting of the substrate through the microfluidic channels. In some embodiments, the liquids include between 0.01% and 5% BSA. In some embodiments, the liquids include between 0.01% and 5% Tween.

Referring again to FIG. 1, the light source 106 is configured to irradiate the surface of the substrate 102. Depending on the signal to be detected, the light source 106 may provide light ranging from the visible range to the near infrared range. Exemplary light sources include lasers and light emitting diodes.

The detector 108 is configured to detect light emitted from the surface of the substrate 102. In some embodiments, detection is achieved by visible, colorimetric, fluorescent or luminescent detection. In some embodiments, detection is achieved by imaging such as by photography or by electronic detectors. Exemplary electronic detectors include photodiodes, charge-coupled device (CCD) detectors, or complementary metal-oxide semiconductor (CMOS) detectors.

The analog signal from the detector 108 is digitized by an analog-to-digital converter 114. The digitized signal is processed by a microprocessor 116 to obtain at least one value or intensity of detected light that is store in memory 118 and/or displayed on an optional display 120.

By using appropriate electronics and software, the system 100 can be programmed to know the identity and location of specific substances (or analytes) bound to the binding agent 110 on the surface of the substrate 102. The identity and location of the analytes can be correlated with signals generated so that the analyte can be determined and identified to the tester. Additionally, statistical software may be included so as to combine and formulate the results from various repetitions and/or dilutions of the sample. In this manner, the signals obtained from a multiplicity of analytes may be factored together and a statistically significant result displayed to the tester.

Methods

Any of the methods described herein may be executed with the aforementioned system illustrated in FIG. 1.

Figure 6:
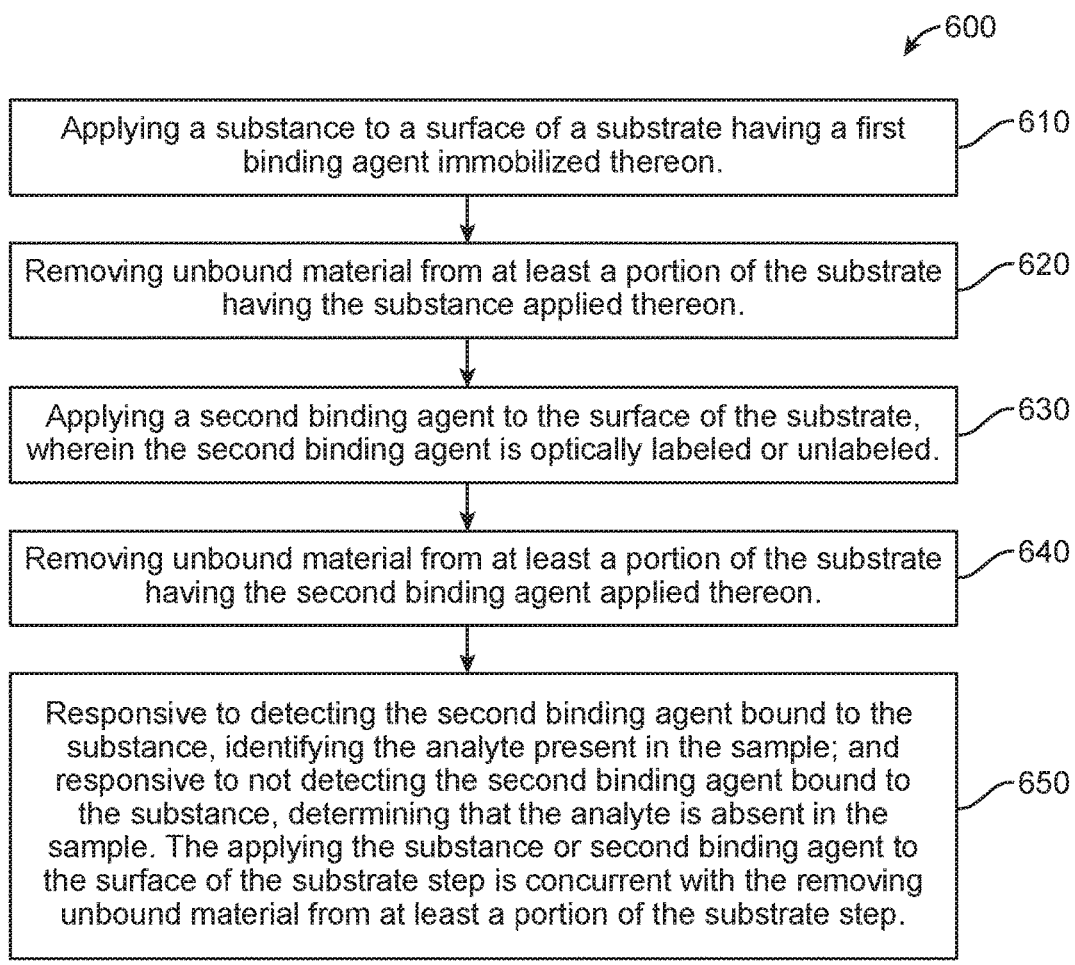
FIG. 6 is a flow chart showing a method of determining the presence or absence of an analyte in a sample using the system of FIG. 1 according to an embodiment of the invention. The method includes applying a substance (e.g., an antigen) to the surface of a substrate having a previously immobilized first binding agent (e.g. an antibody).

Referring to FIG. 6, a method 600 for analyzing samples will now be described.

In exemplary step 610, a substance is applied to a wet or dry surface of a substrate 102 having a first binding agent 110 immobilized thereon. In an embodiment, the first binding agent is capable of binding to the substance. In some embodiments, the first binding agent is a capture antibody from a reagent or a sample and the substance is an antigen from a sample or a reagent, respectively. In some embodiments, after application, the substance may be allowed to incubate with the first binding agent 110 for about 5 minutes to about 60 minutes.

Figure 4:
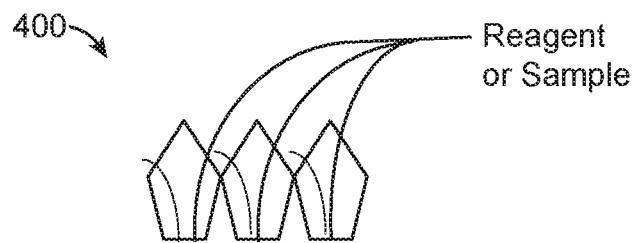
FIG. 4 shows a microfluidic probe having a plurality of processing liquid microchannels which may be connected to a single reagent solution or multiple reagent solutions according to an embodiment of the invention.

In an embodiment, one or more substances are applied with one or more microfluidic probes. In some embodiments, one microfluidic probe is used for each substance (FIG. 2). Each substance is applied to the substrate 102 coated with the first binding agents 110 (i.e., in a direction parallel or perpendicular to the line of the first binding agents 110) such that the substance is applied to each of the binding agents 110 coated on the substrate 102. In yet another embodiment, an array of probes in parallel (probe array 400) is connected to the same or different substances (FIG. 4). The probe array 400 applies the same or different substances to all the binding agents 110 at once. For a new substance, the channels in the probe array 400 are, for example, rinsed to remove the first substance, the probe array 400 is moved together to another set of first binding agents 110, and the new substance is applied to the new set of binding agents 110. For each new substance, the process of rinsing and moving the probe array 400 is repeated. In some embodiments, a plurality of probe arrays 400 are used to test multiple first binding agents 110 each against multiple substances at one time.

In an embodiment shown in FIG. 5, a microfluidic probe 500 includes a plurality of processing liquid microchannels. The plurality of processing liquid microchannels may be used to deposit one or more substances (i.e., the same or different substances) and/or first binding agents 110 onto the surface of the substrate 102. In some embodiments, the microfluidic probe includes 2-50 processing liquid microchannels. In other embodiments, each of the probes in the probe arrays 400 (shown in FIG. 4) include a plurality of microchannels.

In exemplary step 620, unbound material is removed from at least a portion of the substrate 102 having the substance applied thereon.

In exemplary step 630, a second binding agent is applied to the surface of the substrate, wherein the second binding agent is optically labeled or unlabeled. In an embodiment, the second binding agent may be optically labeled or unlabeled primary antibody. In some embodiments, after application, the second binding agent may be allowed to incubate with the material on the surface of the substrate 102 for about 5 minutes to about 60 minutes.

In exemplary step 640, unbound material is removed from at least a portion of the substrate 102 having the second binding agent applied thereon.

In steps 620 and 640, the unbound material may be removed by washing the surface of the substrate 102 with, for example, buffer, water or saline. In embodiments, a microfluidic probe may be used to remove unbound material by pumping a wash solution through one or more processing liquid microchannels. In some embodiments, the wash steps may be performed concurrent with the respective application steps. For example step 610 may be concurrent with step 620 and step 630 may be concurrent with step 640.

In exemplary step 650, the optically labeled second binding agent bound to the substance is detected and the analyte present in the sample is identified. The absence of analyte in the sample may also be determined by not detecting the optically labeled second binding agent bound to the substance.

Unlabeled second binding agent bound to the analyte may also be detected by secondary labeling detection including, for example, fluorescent or chemiluminescent conjugated antibodies. In a secondary labeling detection embodiment, an optically labeled third binding agent (e.g., an optically labeled secondary antibody) is applied to the surface of the substrate having the unlabeled second binding agent bound to the substance. Unbound material is removed by pumping a wash solution through one or more processing liquid microchannels. In an embodiment, the wash step is concurrent with the application of the third binding agent step. The optically labeled third binding agent bound to the second binding agent is then detected and the analyte present in the sample is identified. The absence of analyte in the sample may also be determined by not detecting the optically labeled third binding agent bound to the second binding agent.

Figure 7:
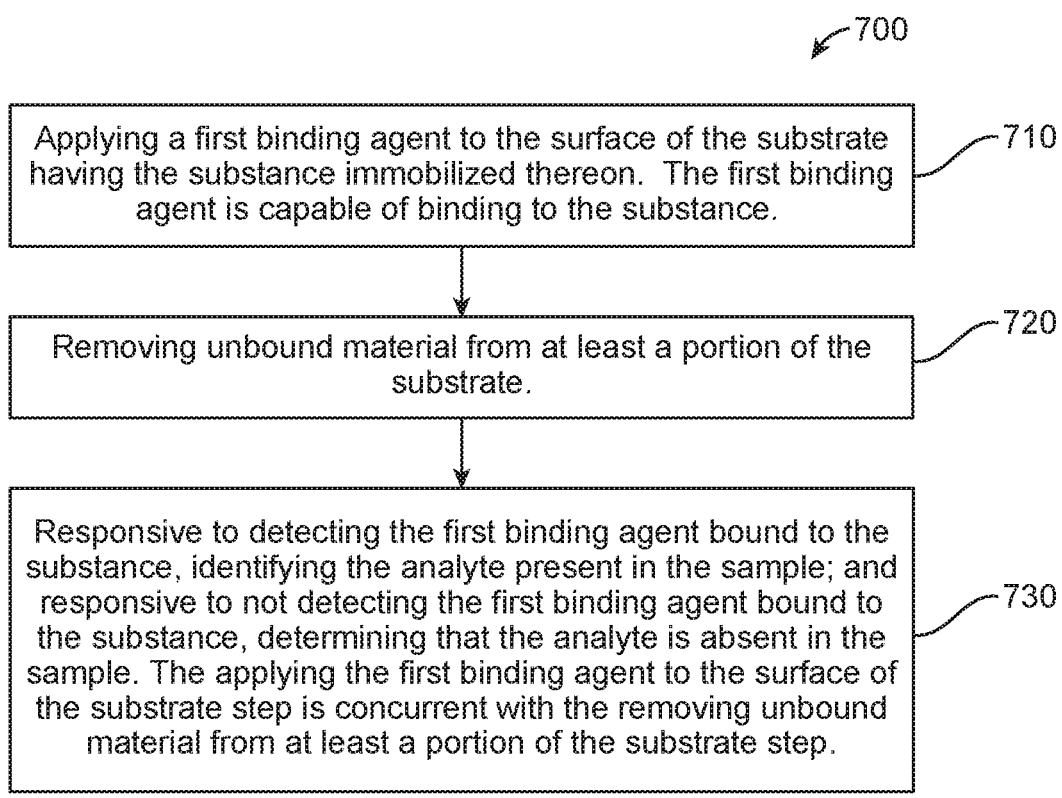
FIG. 7 is a flow chart showing a method of determining the presence or absence of an analyte in a sample using the system of FIG. 1 according to another embodiment of the invention. The method includes applying a first binding agent (e.g. an antibody) to the surface of a substrate having a previously immobilized substance (e.g., an antigen).

As illustrated in FIG. 7, a method 700 for analyzing samples will now be described.

In exemplary step 710, a first binding agent is applied to the surface of a substrate having a substance immobilized thereon. In an embodiment, the first binding agent is capable of binding to the substance and is optically labeled or unlabeled. In some embodiments, the first binding agent is labeled or unlabeled primary antibody and the substance is an antigen from a sample or a reagent. In some embodiments, after application, the first binding agent may be allowed to incubate with the substance for about 5 minutes to about 60 minutes.

In an embodiment, the first binding agent is applied to the surface of the substrate 102 with one or more microfluidic probes 200. In another embodiment, probe array 400 (FIG. 4) is used to apply one or more first binding agents to the surface of the substrate 102. In yet another embodiment, the microfluidic probe 500 (FIG. 5) having more than one microchannels is used to apply one or more first binding agents to the surface of the substrate 102.

In exemplary step 720, the unbound material is removed by pumping a wash solution through one or more processing liquid microchannels of a microfluidic probe. In an embodiment, the wash step 720 is concurrent with the application step 710.

In exemplary step 730, optically labeled first binding agent bound to the substance is detected and the analyte present in the sample is identified. The absence of analyte in the sample may also be determined by not detecting the optically labeled first binding agent bound to the substance.

Unlabeled first binding agent bound to the analyte may also be detected by secondary labeling detection. In a secondary labeling detection embodiment, an optically labeled third binding agent (e.g., an optically labeled secondary antibody) is applied to the surface of the substrate having the second binding agent bound to the substance. Unbound material is removed by pumping a wash solution through one or more processing liquid microchannels. In an embodiment, the wash step is concurrent with the application of the third binding agent step. The optically labeled third binding agent bound to the second binding agent is then detected and the analyte present in the sample is identified. The absence of analyte in the sample may also be determined by not detecting the optically labeled third binding agent bound to the second binding agent.

Figure 8:
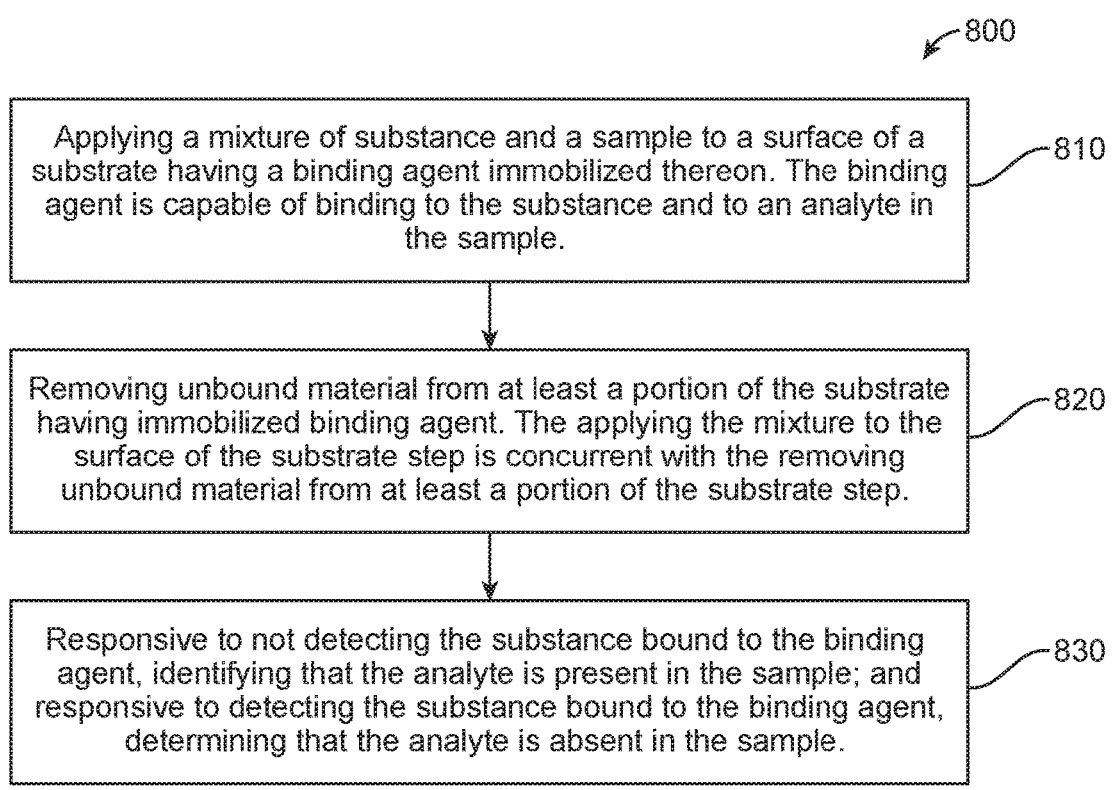
FIG. 8 is a flow chart showing a method of determining the presence or absence of an analyte in a sample using the system of FIG. 1 according to another embodiment of the invention. The method includes applying a mixture of a sample having an analyte (e.g., an antigen) and a substance (e.g., a purified and labeled version of the analyte) to a surface of a substrate having a previously immobilized binding agent. The binding agent is capable of binding to the substance and the analyte.

Referring to FIG. 8, a method 800 for analyzing samples will now be described.

In exemplary step 810, a mixture of a substance and a sample having an analyte is applied to a surface of a substrate having a binding agent immobilized thereon. In some embodiments, the binding agent is capable of binding to the substance and to the analyte. In an embodiment, the binding agent is an antibody, the sample is an analyte (e.g., an antigen) and the substance is an optically labeled and purified form of the analyte in the sample. In embodiments, the analyte and substance compete for the same binding site on the binding agent such that higher amounts of analyte in the sample result in less of the optically labeled substance being detected (i.e., there is an inverse relationship between the amount of signal detected and the amount of analyte in the sample). In some embodiments, after application, the mixture may be allowed to incubate with the binding agent for about 5 minutes to about 60 minutes.

In an embodiment, the mixture is applied to the surface of the substrate 102 with one or more microfluidic probes 200. In another embodiment, probe array 400 (FIG. 4) is used to apply one or more mixtures to the surface of the substrate 102. In yet another embodiment, the microfluidic probe 500 (FIG. 5) having more than one microchannels is used to apply one or more mixtures to the surface of the substrate 102.

In exemplary step 820, the unbound material is removed by pumping a wash solution through one or more processing liquid microchannels of a microfluidic probe. In an embodiment, the wash step 820 is concurrent with the application step 810.

In exemplary step 830, optically labeled substance bound to the binding agent is not detected and the analyte present in the sample is identified. The absence of analyte in the sample may also be determined by detecting the optically labeled substance bound to the binding agent.

Computer Implemented Methods and Systems

Any of the methods described herein may be totally or partially performed with a computer system including one or more processors, which can be configured to perform the steps of the methods. Thus, embodiments can be directed to computer systems configured to perform the steps of any of the methods described herein, potentially with different components performing a respective step or a respective group of steps. Although presented as numbered or ordered steps, steps of the methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

In some embodiments, the computer implemented method is implemented by a computer system that is in electronic communication with an image scanner that is capable of detecting optically labeled binding agents bound to, for example, a substance on a substrate or in an image of a substrate.

The disclosure further provides a computer product that is capable of performing any one of or all of the steps of the methods described herein. Thus, in some embodiments, the computer product comprises a non-transitory computer readable medium storing a plurality of instructions for controlling a processor to perform an operation of one or more of the method steps described herein.

Figure 9:
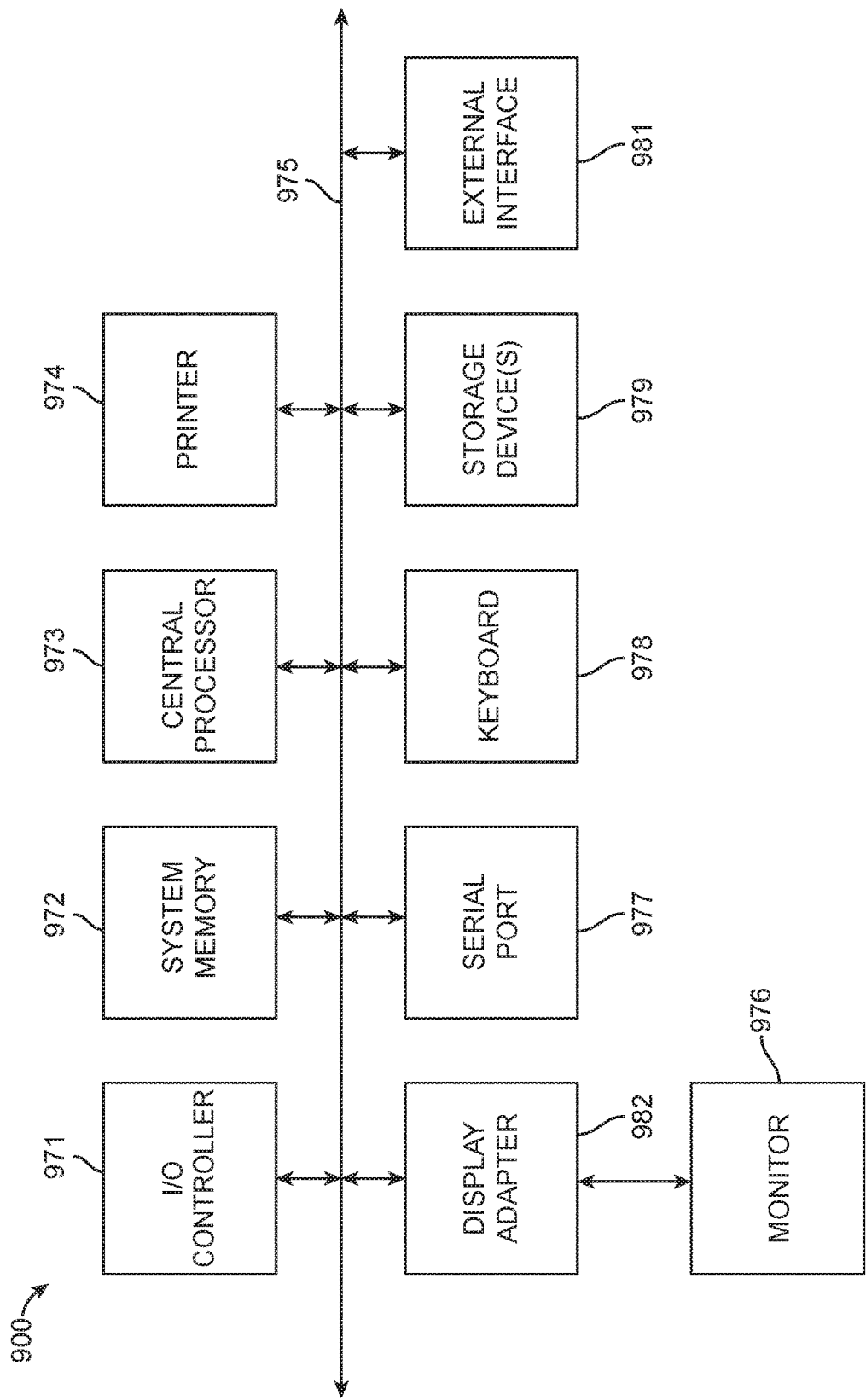
FIG. 9 shows a block diagram of an example computer system usable with the systems and methods according to embodiments of the invention.

FIG. 9 shows a block diagram of an example computer system 900 usable with system and methods according to embodiments of the present disclosure.

Any of the computer systems mentioned herein may utilize any suitable number of subsystems. Examples of such subsystems are shown in FIG. 9 in computer apparatus 900. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 9 are interconnected via a system bus 975. Additional subsystems such as a printer 974, a keyboard 978, a storage device(s) 979, a monitor 976, which is coupled to a display adapter 982, and others are shown. Peripherals and input/output (I/O) devices, which couple to I/O controller 971, can be connected to the computer system by any number of means known in the art, such as a serial port 977. For example, the serial port 977 or an external interface 981 (e.g. Ethernet, Wi-Fi, etc.) can be used to connect the computer system 900 to a wide area network such as the Internet, a mouse input device, or a scanner. The interconnection via the system bus 975 allows the central processor 973 to communicate with each subsystem and to control the execution of instructions from the system memory 972 or the storage device(s) 979 (e.g., a fixed disk, such as a hard drive or optical disk), as well as the exchange of information between subsystems. The system memory 872 and/or the storage device(s) 979 may embody a computer readable medium. Any of the data mentioned herein can be output from one component to another component and can be output to the user.

A computer system can include a plurality of the same components or subsystems, e.g., connected together by the external interface 981 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that the embodiments described above can be implemented in the form of control logic using hardware (e.g. an application specific integrated circuit or field programmable gate array) and/or using computer software with a generally programmable processor in a modular or integrated manner. As used herein, a processor includes a multi-core processor on a same integrated chip, or multiple processing units on a single circuit board or networked. Based on the disclosure and teachings provided herein, a person of ordinary skill in the art will know and appreciate other ways and/or methods to implement embodiments described herein using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present disclosure may be created using a data signal encoded with such programs. Computer readable media encoded with the program code may be packaged with a compatible device or provided separately from other devices (e.g., via Internet download). Any such computer readable medium may reside on or within a single computer product (e.g. a hard drive, a CD, or an entire computer system), and may be present on or within different computer products within a system or network. A computer system may include a monitor, printer, or other suitable display for providing any of the results mentioned herein to a user.

Additional Disclosure and Claimable Subject Matter

Item 1. A method of determining the presence or absence of an analyte in a sample, the method comprising:
applying a substance to a surface of a substrate having a first binding agent immobilized thereon, wherein the first binding agent is capable of binding to the substance;
removing unbound material from at least a portion of the substrate having the substance applied thereon;
applying a second binding agent to the surface of the substrate, wherein the second binding agent is optically labeled or unlabeled;
removing unbound material from at least a portion of the substrate having the second binding agent applied thereon;
responsive to detecting an optically labeled second binding agent bound to the substance, identifying the analyte present in the sample; and
responsive to not detecting the optically labeled second binding agent bound to the substance, determining that the analyte is absent in the sample,
wherein the applying the substance or second binding agent to the surface of the substrate steps are concurrent with the respective removing unbound material from at least a portion of the substrate steps.

Item 2. The method of Item 1, further comprising:
applying a third binding agent to the surface of the substrate having the second binding agent bound to the substance, wherein the third binding agent is optically labeled and the second binding agent is optically unlabeled;
removing unbound material from at least a portion of the substrate having the third binding agent applied thereon;
responsive to detecting an optically labeled third binding agent bound to the second binding agent, identifying the analyte present in the sample; and
responsive to not detecting the optically labeled third binding agent bound to the second binding agent, determining that the analyte is absent in the sample,
wherein the applying the third binding agent to the surface of the substrate step is concurrent with the removing unbound material from at least a portion of the substrate step.

Item 3. The method of Item 1 or 2, wherein the applying the substance or second binding agent to the surface of the substrate step comprises dispensing a microfluidic volume of the substance or second binding agent.

Item 4. The method of Item 1 or 2, wherein the applying the substance or second binding agent to the surface of the substrate step comprises dispensing a sub-microfluidic volume of the substance or second binding agent.

Item 5. The method of Item 1 or 2, wherein the applying the substance or second binding agent to the surface of the substrate and the removing unbound material from at least a portion of the substrate steps are performed with a hydrodynamic flow confinement dispenser.

Item 6. The method of Item 5, wherein the dispenser is a microfluidic probe.

Item 7. The method of Item 5, wherein the dispenser is a microfluidic probe having a plurality of microchannels.

Item 8. The method of Item 5, wherein the dispenser is an array of microfluidic probes.

Item 9. The method of any one of previous Items 1 to 8, wherein the surface of the substrate is wet.

Item 10. The method of any one of previous Items 1 to 9, wherein the applying the substance or second binding agent to the surface of the substrate step comprises dispensing the substance or second binding agent in at least one discreet path.

Item 11. The method of Item 10, wherein the path is a straight line.

Item 12. The method of Item 10, wherein the path is from between 25 nanometers to 500 micrometers wide.

Item 13. The method of any one of previous Items 1 to 9, wherein the applying the substance or second binding agent to the surface of the substrate step comprises dispensing the substance or second binding agent in at least one discreet spot between 25 nanometers and 500 micrometers in diameter.

Item 14. The method of any one of previous Items 1 to 13, wherein the first binding agent is immobilized in at least one discreet spot.

Item 15. The method of any one of previous Items 1 to 13, wherein the first binding agent is immobilized in at least one discreet line.

Item 16. The method of any one of previous Items 1 to 15, wherein the first binding agent is 1-100 different first binding agents.

Item 17. The method of any one of previous Items 1 to 16, wherein the substance is 1-100 different substances.

Item 18. The method of any one of previous Items 1 to 17, wherein the first binding agent comprises an antibody or antibody fragment from a reagent or a sample.

Item 19. The method of Item 18, wherein the sample is selected from the group consisting of cell extract, whole blood, plasma, serum, saliva, urine, milk, eggs and water.

Item 20. The method of Item 18, wherein the sample includes an analyte selected from the group consisting of hormones, proteins, peptides, antibodies and antibody fragments.

Item 21. A system comprising:
a substrate having a first binding agent immobilized in discreet locations thereon, wherein the first binding agent is capable of binding to a substance applied to the surface of the substrate;
a dispenser configured to simultaneously dispense the substance or at least one binding agent onto the substrate and to remove unbound material from the substrate; and
a detector configured to detect the presence or absence of the at least one binding agent.

Item 22. The system of Item 21, wherein the dispenser is a microfluidic probe.

Item 23. The system of Item 21, wherein the dispenser is an array of microfluidic probes.

Item 24. The system of Item 21, wherein the dispenser is a microfluidic probe having a plurality of microchannels.

Item 25. A method of determining the presence or absence of an analyte in a sample, the method comprising:
applying a first binding agent to the surface of the substrate having a substance immobilized thereon, wherein the first binding agent is capable of binding to the substance and is optically labeled or unlabeled;
removing unbound material from at least a portion of the substrate having the first binding agent applied thereon; and
responsive to detecting an optically labeled first binding agent bound to the substance, identifying the analyte present in the sample; and
responsive to not detecting the optically labeled first binding agent bound to the substance, determining that the analyte is absent in the sample;
wherein the applying the first binding agent to the surface of the substrate step is concurrent with the removing unbound material from at least a portion of the substrate step.

Item 26. The method of Item 25, further comprising:
applying a second binding agent to the surface of the substrate having a first binding agent bound to the substance, wherein the second binding agent is optically labeled and the first binding agent is optically unlabeled;
removing unbound material from at least a portion of the substrate having the second binding agent applied thereon;
responsive to detecting the second binding agent bound to the first binding agent, identifying the analyte present in the sample; and
responsive to not detecting the second binding agent bound to the first binding agent, determining that the analyte is absent in the sample.

Item 27. The method of Item 25 or 26, wherein the applying the first binding agent to the surface of the substrate step comprises dispensing a microfluidic volume of the substance or second binding agent.

Item 28. The method of Item 25 or 26, wherein the applying the first binding agent to the surface of the substrate step comprises dispensing a sub-microfluidic volume of the substance or second binding agent.

Item 29. The method of Item 25 or 26, wherein the applying the first binding agent to the surface of the substrate and the removing unbound material from at least a portion of the substrate steps are performed with a hydrodynamic flow confinement dispenser.

Item 30. The method of any one of previous Items 25 to 29, wherein the dispenser is a microfluidic probe.

Item 31. The method of any one of previous Items 25 to 29, wherein the dispenser is a microfluidic probe having a plurality of microchannels.

Item 32. The method of any one of previous Items 25 to 29, wherein the dispenser is an array of microfluidic probes.

Item 33. The method of any one of previous Items 25 to 32, wherein the surface of the substrate is wet.

Item 34. The method of any one of previous Items 25 to 33, wherein the applying the first binding agent to the surface of the substrate step comprises dispensing the first binding agent in at least one discreet path.

Item 35. The method of Item 34, wherein the path is a straight line.

Item 36. The method of Item 34, wherein the path is from between 25 nanometers to 500 micrometers wide.

Item 37. The method of claim 25, wherein the applying the first binding agent to the surface of the substrate step comprises dispensing the first binding agent in at least one discreet spot between 25 nanometers and 500 micrometers in diameter.

Item 38. The method of any one of previous Items 25 to 33, wherein the substance is immobilized in at least one discreet spot.

Item 39. The method of any one of previous Items 25 to 33, wherein the substance is immobilized in at least one discreet line.

Item 40. The method of any one of previous Items 25 to 39, wherein the substance is 1-100 different substances.

Item 41. The method of any one of previous Items 25 to 40, wherein the first binding agent is 1-100 different first binding agents.

Item 42. The method of any one of previous Items 25 to 41, wherein the substance comprises an antigen from a reagent or a sample.

Item 43. The method of Item 42, wherein the sample is selected from the group consisting of cell extract, whole blood, plasma, serum, saliva, urine, milk, eggs and water.

Item 44. The method of Item 43, wherein the sample includes an analyte selected from the group consisting of hormones, proteins, peptides, antibodies and antibody fragments.

Item 45. A system comprising:
  a substrate having a substance immobilized in discreet locations, wherein an first binding agent is capable of binding to the substance;
  a dispenser configured to simultaneously dispense at least one binding agent onto the substrate and to remove unbound material from the substrate; and
  a detector configured to detect the presence or absence of the at least one binding agent.

Item 46. The system of Item 45, wherein the dispenser is a microfluidic probe.

Item 47. The system of Item 45, wherein the dispenser is an array of microfluidic probes.

Item 48. The system of Item 45, wherein the dispenser is a microfluidic probe having a plurality of microchannels.

Item 49. A method of determining the presence or absence of an analyte in a sample, the method comprising:
  applying a mixture of a substance and a sample having an analyte to a surface of a substrate having a binding agent immobilized thereon, wherein the binding agent is capable of binding to the substance and the analyte;
  removing unbound material from at least a portion of the substrate having the binding agent immobilized thereon; and
  responsive to not detecting the substance bound to the binding agent, identifying the analyte present in the sample; and
  responsive to detecting the substance bound to the binding agent, determining that the analyte is absent in the sample;
  wherein the applying the mixture to the surface of the substrate step is concurrent with the removing unbound material from at least a portion of the substrate step.

Item 50. The method of Item 49, wherein the applying the mixture to the surface of the substrate step comprises dispensing a microfluidic volume of the mixture.

Item 51. The method of Item 49, wherein the applying the mixture to the surface of the substrate step comprises dispensing a sub-microfluidic volume of the mixture.

Item 52. The method of any one of previous Items 49 to 51, wherein the applying the mixture to the surface of the substrate and the removing unbound material from at least a portion of the substrate steps are performed with a hydrodynamic flow confinement dispenser.

Item 53. The method of Item 52, wherein the dispenser is a microfluidic probe.

Item 54. The method of Item 52, wherein the dispenser is a microfluidic probe having a plurality of microchannels.

Item 55. The method of Item 52, wherein the dispenser is an array of microfluidic probes.

Item 56. The method of any one of previous Items 49 to 55, wherein the surface of the substrate is wet.

Item 57. The method of any one of previous Items 49 to 56, wherein the applying the mixture to the surface of the substrate step comprises dispensing the substance in at least one discreet path.

Item 58. The method of Item 57, wherein the path is a straight line.

Item 59. The method of Item 57, wherein the path is from between 25 nanometers to 500 micrometers wide.

Item 60. The method of any one of previous Items 49 to 56, wherein the applying the mixture to the surface of the substrate step comprises dispensing the mixture in at least one discreet spot between 25 nanometers and 500 micrometers in diameter.

Item 61. The method of any one of previous Items 49 to 60, wherein the binding agent is immobilized in at least one discreet spot.

Item 62. The method of any one of previous Items 49 to 60, wherein the binding agent is immobilized in at least one discreet line.

Item 63. The method of any one of previous Items 49 to 62, wherein the binding agent is 1-100 different binding agents.

Item 64. The method of any one of previous Items 49 to 63, wherein the mixture is 1-100 different mixtures.

Item 65. The method of any one of previous Items 49 to 64, wherein the binding agent comprises an antibody or antibody fragment.

Item 66. The method of any one of previous Items 49 to 65, wherein the sample is selected from the group consisting of cell extract, whole blood, plasma, serum, saliva, urine, milk, eggs and water.

Item 67. The method of Item 66, wherein the sample includes an analyte selected from the group consisting of hormones, proteins, peptides, antibodies and antibody fragments.

Item 68. The method of any one of previous Items 49 to 67, wherein the substance is a purified and optically labeled analyte selected from the group consisting of hormones, proteins, and peptides.

Item 69. A system comprising:
  a substrate having a binding agent immobilized in discreet locations, wherein the binding agent is capable of binding to an analyte in a sample and to a substance;
  a dispenser configured to simultaneously dispense a mixture of the sample and the substance onto the substrate and to remove unbound material from the substrate; and
  a detector configured to detect the presence or absence of the analyte in the sample bound to the binding agent.

Item 70. The system of Item 69, wherein the dispenser is a microfluidic probe.

Item 71. The system of Item 69, wherein the dispenser is an array of microfluidic probes.

Item 72. The system of Item 69, wherein the dispenser is a microfluidic probe having a plurality of microchannels.

EXAMPLES

Example 1: ELISA Using a Microfluidic Probe

The following describes one proposed method for a sandwich ELISA using the microfluidic probes to detect mouse IL-12 protein from plasma on a single PVDF membrane.

A pre-wetted (coating buffer; Invitrogen; CB01100) low fluorescent PVDF membrane is mounted to a X-Y-Z platform in the microfluidic probe sample analysis system. For the coating of capture antibody onto the membrane, a rat monoclonal antibody against mouse IL-12 (Invitrogen; AMC0124D) is diluted to a concentration of 1 µg/ml with a coating buffer. A microfluidic probe is used to coat the capture antibody onto the membrane in predetermined spots, each 25-500 micrometers in diameter, in eight rows and 12 columns totaling 96 locations. Concurrent with the dispensing step, unbound material is removed by the microfluidic probe.

Immediately thereafter, or after 5 minutes to overnight incubation, blocking buffer (Invitrogen; DS98200) is dispensed with the probe to each spot and excess material is removed.

Immediately thereafter, or after 5 minutes to 1 hour of incubation, recombinant mouse IL-12 protein standard (Invitrogen; SD041) is reconstituted in assay buffer to 500 pg/ml and six 1:2 serial dilutions are prepared, plus one buffer only zero standard control. In a similar fashion, the plasma samples from five mice (3 treated and 2 untreated) are prepared by seven 1:2 serial dilutions. The standards and samples are dispensed in duplicates onto the membrane with microfluidic probes in a vertical fashion starting at the bottom row with the lowest sample dilution and the buffer only control, respectively.

As a next step, rat anti-mouse interleukin-12 (IL-12) biotin labeled detection antibody (Invitrogen; AMC9129D) is diluted to 0.125 μg/mL with Assay Buffer supplemented with 5% calf serum (Invitrogen; DS98200), and then dispensed in each of the 96 spots on the membrane with a microfluidic probe. Immediately thereafter, or after 5 minutes to 2 hours of incubation, unbound material is removed and each spot is washed by dispensing washing buffer (Invitrogen; WB01).

To detect the amount of IL-12 in each sample, working streptavidin-HRP solution (Invitrogen; SNN4004Y) is added with a microfluidic probe to each spot. Immediately thereafter, or after 5 minutes to 30 minutes of incubation, unbound material is removed and each spot is washed by dispensing washing buffer. The TMB substrate solution (Cat. # SB01) is then added with a microfluidic probe to each spot and after a 5 minute to 30 minute incubation period in the dark at room temperature, Stop Solution (Invitrogen; SS03100) is added to each spot with a microfluidic probe. A colorimetric imager is then used within 30 minutes of adding Stop Solution for detection of all 96 spots on the membrane. The IL-12 concentration is calculated for each sample using a log-log or 4-parameter curve fit.

In the claims appended hereto, the term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method of determining the presence or absence of an analyte in a sample, the method comprising:
    applying a substance to a surface of a substrate having a first binding agent immobilized thereon, wherein the first binding agent is capable of binding to the substance;
    removing unbound material from at least a portion of the substrate having the substance applied thereon;
    applying a second binding agent to the surface of the substrate, wherein the second binding agent is optically labeled or unlabeled;
    removing unbound material from at least a portion of the substrate having the second binding agent applied thereon; and either
    responsive to detecting the second binding agent bound to the substance, identifying the analyte present in the sample; or
    responsive to not detecting the second binding agent bound to the substance, determining that the analyte is absent in the sample,
    wherein the applying the substance or second binding agent to the surface of the substrate steps are concurrent with the respective removing unbound material from at least a portion of the substrate steps.

2. The method of claim 1, further comprising:
    applying a third binding agent to the surface of the substrate having the second binding agent bound to the substance, wherein the third binding agent is optically labeled and the second binding agent is optically unlabeled;
    removing unbound material from at least a portion of the substrate having the third binding agent applied thereon; and
    responsive to detecting an optically labeled third binding agent bound to the second binding agent, identifying the analyte present in the sample; or
    responsive to not detecting the optically labeled third binding agent bound to the second binding agent, determining that the analyte is absent in the sample,
    wherein the applying the third binding agent to the surface of the substrate step is concurrent with the removing unbound material from at least a portion of the substrate step.

3. The method of claim 1, wherein the applying the substance or second binding agent to the surface of the substrate step comprises dispensing a microfluidic volume of the substance or second binding agent.

4. The method of claim 1, wherein the applying the substance or second binding agent to the surface of the substrate step comprises dispensing a sub-microfluidic volume of the substance or second binding agent.

5. The method of claim 1, wherein the applying the substance or second binding agent to the surface of the substrate and the removing unbound material from at least a portion of the substrate steps are performed with a hydrodynamic flow confinement dispenser.

6. The method of claim 5, wherein the dispenser is a microfluidic probe.

7. The method of claim 5, wherein the dispenser is a microfluidic probe having a plurality of microchannels.

8. The method of claim 5, wherein the dispenser is an array of microfluidic probes.

9. The method of claim 1, wherein the surface of the substrate is wet.

10. The method of claim 1, wherein the applying the substance or second binding agent to the surface of the substrate step comprises dispensing the substance or second binding agent in at least one discreet path.

11. The method of claim 10, wherein the path is a straight line.

12. The method of claim 10, wherein the path is from between 25 nanometers to 500 micrometers wide.

13. The method of claim 1, wherein the applying the substance or second binding agent to the surface of the substrate step comprises dispensing the substance or second binding agent in at least one discreet spot between 25 nanometers and 500 micrometers in diameter.

14. The method of claim 1, wherein the first binding agent is immobilized in at least one discreet spot.

15. The method of claim 1, wherein the first binding agent is immobilized in at least one discreet line.

16. The method of claim 1, wherein the first binding agent is 1-100 different first binding agents.

17. The method of claim 1, wherein the substance is 1-100 different substances.

18. The method of claim 1, wherein the first binding agent comprises an antibody or antibody fragment from a reagent or a sample.

19. The method of claim 18, wherein the sample is selected from the group consisting of cell extract, whole blood, plasma, serum, saliva, urine, milk, eggs and water.

20. The method of claim 18, wherein the sample includes an analyte selected from the group consisting of hormones, proteins, peptides, antibodies and antibody fragments.

* * * * *